US011147641B2

(12) United States Patent
Hashimoto et al.

(10) Patent No.: US 11,147,641 B2
(45) Date of Patent: Oct. 19, 2021

(54) ROBOT SYSTEM

(71) Applicant: KAWASAKI JUKOGYO KABUSHIKI KAISHA, Kobe (JP)

(72) Inventors: Yasuhiko Hashimoto, Kobe (JP); Masayuki Kamon, Akashi (JP); Shigetsugu Tanaka, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 213 days.

(21) Appl. No.: 15/755,246

(22) PCT Filed: May 27, 2016

(86) PCT No.: PCT/JP2016/002591
§ 371 (c)(1),
(2) Date: Feb. 26, 2018

(87) PCT Pub. No.: WO2017/033364
PCT Pub. Date: Mar. 2, 2017

(65) Prior Publication Data
US 2018/0250825 A1 Sep. 6, 2018

(30) Foreign Application Priority Data
Aug. 25, 2015 (JP) .............................. JP2015-165479

(51) Int. Cl.
G05B 19/418 (2006.01)
A61B 34/37 (2016.01)
(Continued)

(52) U.S. Cl.
CPC .............. A61B 34/37 (2016.02); A61B 34/32 (2016.02); B23P 19/04 (2013.01); B23Q 15/12 (2013.01);
(Continued)

(58) Field of Classification Search
CPC ......... A61B 34/37; A61B 34/32; A61B 34/35; A61B 34/70; G05B 19/4182;
(Continued)

(56) References Cited

U.S. PATENT DOCUMENTS

2005/0004707 A1   1/2005 Kazi et al.
2011/0060443 A1*  3/2011 Schwarm ............. G05B 13/042
                                             700/104

(Continued)

FOREIGN PATENT DOCUMENTS

JP   H08-267381 A   10/1996
JP   2003-311661 A  11/2003
JP   2004-299049 A  10/2004

OTHER PUBLICATIONS

Fong, Terrence. "Collaborative Control: A Robot-Centric Model for Vehicle Teleoperation". The Robotics Institute Carnegie Mellon University, pp. 25-40, Chapter 3, 2001.

(Continued)

Primary Examiner — Harry Y Oh
Assistant Examiner — Sohana Tanju Khayer
(74) Attorney, Agent, or Firm — Oliff PLC

(57) ABSTRACT

A robot system including a master device configured to receive a manipulating instruction from an operator and transmit the received manipulating instruction as a manipulating input signal, a plurality of slave robots configured to operate according to the manipulating input signal transmitted from the master device, a management control device configured to manage operations of the plurality of slave robots, respectively, and an output device configured to output information transmitted from the management control device. The management control device determines a priority of transmitting the manipulating input signal from the master device to the slave robot among the plurality of slave robots that are in a standby state of the manipulating (Continued)

input signal, and transmits information related to the determined priority to the output device. Thus, the operator is able to efficiently transmit the manipulating input signal to the plurality of slave robots through the master device.

5 Claims, 8 Drawing Sheets

(51) Int. Cl.
| | |
|---|---|
| B25J 9/00 | (2006.01) |
| B25J 9/16 | (2006.01) |
| B23P 19/04 | (2006.01) |
| B25J 13/00 | (2006.01) |
| B25J 19/04 | (2006.01) |
| B25J 13/08 | (2006.01) |
| B25J 3/00 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1638* (2013.01); *B25J 9/1641* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ......... G05B 2219/40143; G05B 2219/39004; G05B 2219/40182; G05B 2219/40145; G05B 2219/40387; G05B 2219/40139; G05B 2219/40161; G05B 2219/40146; G05B 2219/40627; G05B 2219/40162; G05B 2219/40136; G05B 2219/39439; G05B 2219/40022; G05B 2219/39531; G05B 2219/40163; G05B 2219/39533; G05B 2219/35464; G05B 2219/40142; G05B 2219/33007; G05B 2219/40169; G05B 2219/40183; G05B 2219/40134; G05B 2219/40195; G05B 2219/37297; G05B 2219/39102; G06T 7/62; G06T 7/70; B25J 9/0081; B25J 9/1646; B25J 9/1653; B25J 9/1674; B25J 9/1612; B25J 19/028; B25J 9/1602; B25J 13/085; B25J 13/087; B25J 9/1697; B25J 13/006; B25J 9/1689; B25J 19/023; B25J 3/04; B25J 9/1633; B25J 9/1628; B25J 13/02; B25J 9/163; B25J 11/008; B25J 13/003; B25J 13/065; B25J 13/025; B25J 13/084; B25J 11/005; B25J 9/1661; B25J 9/1692; B25J 13/08; B25J 9/0087; B25J 3/00; B25J 9/1669; B25J 9/126; B25J 19/02; B25J 19/06; B25J 13/06; B25J 13/088; B25J 18/00; B25J 9/161; B25J 9/1664; B25J 9/1682; B25J 13/00; B25J 19/04; B23Q 15/12; G06F 3/017; B23P 21/002; B23P 21/00; B23P 19/04; Y10S 901/09; Y10S 901/47; Y10S 901/08; Y10S 901/03; Y10S 901/27; Y10S 901/41; Y10S 901/10; Y10S 901/46; Y10S 901/02; H04N 5/23219; H04N 7/181
See application file for complete search history.

(56) References Cited

U.S. PATENT DOCUMENTS

| | | | |
|---|---|---|---|
| 2012/0041599 A1 | 2/2012 | Townsend et al. | |
| 2012/0150352 A1* | 6/2012 | Park | B25J 13/006 700/264 |
| 2012/0309261 A1* | 12/2012 | Boman | A63H 30/04 446/268 |
| 2013/0085625 A1* | 4/2013 | Wolfe | G06F 19/00 701/1 |

(56) References Cited

U.S. PATENT DOCUMENTS

| | | | |
|---|---|---|---|
| 2014/0067128 A1* | 3/2014 | Kowalski | G05B 19/409 |
| | | | 700/264 |
| 2016/0129592 A1* | 5/2016 | Saboo | G05D 1/0297 |
| | | | 700/248 |
| 2017/0028549 A1* | 2/2017 | Battisti | G05B 19/427 |

OTHER PUBLICATIONS

Fong, Terrence et al. "Collaboration, Dialogue, and Human-Robot Interaction". 10th International Symposium of Robotics Research, pp. 1-10, 2001.

* cited by examiner

| PERFORMING ORDER | ⟨1⟩ | ⟨2⟩ | ⟨3⟩ | ⟨4⟩ | ⟨5⟩ |
|---|---|---|---|---|---|
| OPERATION MODE | AUTOMATIC | MANUAL | AUTOMATIC | MANUAL | AUTOMATIC |
| OPERATION OF SLAVE ARM | EXTRACT WORKPIECE A → MOVE TO ASSEMBLING PREPARATION POS. → OPERATION STANDBY STATE | ASSEMBLE WORKPIECE A ACCORDING TO MANIPULATING INPUT OF OPERATOR | EVACUATE FROM ASSEMBLING COMPLETED POS. → EXTRACT WORKPIECE B → MOVE TO ASSEMBLING PREPARATION POS. → OPERATION STANDBY STATE | ASSEMBLE WORKPIECE B ACCORDING TO MANIPULATING INPUT OF OPERATOR | EVACUATE FROM ASSEMBLING COMPLETED POS. → MOVE TO ALL WORK COMPLETED POS. |
| OPERATION OF OPERATOR | | MANIPULATING INPUT (MANIPULATION OF MASTER ARM) → NOTIFY ASSEMBLING WORK COMPLETION | | MANIPULATING INPUT (MANIPULATION OF MASTER ARM) → NOTIFY ASSEMBLING WORK COMPLETION | |

FIG. 3

ROBOT SYSTEM

TECHNICAL FIELD

The present disclosure relates to a robot system utilizing a master-slave type robot.

BACKGROUND ART

In order to automate works, and achieve manpower saving or an increase in work efficiency, developments of industrial robots have been advanced. For example, the industrial robots are installed in a factory etc. as robots which carry out carrying, assembling, etc. of assembling components (workpieces). Here, when the assembling of the assembling component is automatically carried out by the robot, it requires a mechanism and a control for measuring a spatial relationship between the assembling component and an assembled component (a product) by a sensor, and matching the position and posture of the robot with sufficient accuracy.

Especially, when the assembling component or the assembled component is a large-sized component, it is necessary to enable the robot to accurately grasp a spatial relationship between the robot and the assembling component, or a spatial relationship between the assembling component and the assembled component in order to make the robot automatically perform the assembling work of the assembling component. Moreover, a large number of sensors are required in order to accurately grasp the spatial relationship between the robot and the assembling component, or the spatial relationship between the assembling component and the assembled component. Further, an advanced sensor recognition technology which enables highly-precise measurements in an extensive workspace is also required.

In such a case where the advanced sensor recognition technology is required, it is suitable to switch from an automatic operation to a manual operation in which the robot is capable of performing a work according to manipulating instructions from an operator. Thus, it is important to switch between the automatic operation and the manual operation of the robot at a suitable timing according to the contents of work. For example, Patent Document 1 proposes a robot manual feed control device which is provided with a state display lamp capable of displaying a state of the automatic operation or the manual operation. The robot manual feed control device disclosed in Patent Document 1 is capable of terminating the manual operation mode by an operator monitoring the status display lamp to check a switchable state to the automatic operation mode and pushing an operation button of the manual operation mode.

REFERENCE DOCUMENT OF CONVENTIONAL ART

Patent Document

Patent Document 1: JP1996-267381A

DESCRIPTION OF THE DISCLOSURE

Problems to be Solved by the Disclosure

One purpose of the present disclosure is to provide a robot system in which an operator is able to efficiently transmit a manipulating input signal to a plurality of slave robots through a master device.

SUMMARY OF THE DISCLOSURE

In order to solve the problem described above, a robot system according to one aspect of the present disclosure includes a master device configured to receive a manipulating instruction from an operator and transmit the received manipulating instruction as a manipulating input signal, a plurality of slave robots configured to operate according to the manipulating input signal transmitted from the master device, a management control device configured to manage operations of the plurality of slave robots, respectively, and an output device configured to output information transmitted from the management control device. The management control device determines a priority of transmitting the manipulating input signal from the master device to the slave robot among the plurality of slave robots that are in a standby state of the manipulating input signal, and transmits information related to the determined priority to the output device.

Here, the manipulating input signal is the manipulating input signal transmitted through the master device to the slave robot when the slave robot is operated manually by the operator. In some cases, the manipulating input signal may be included in the manipulating input signal which the slave robot stands by.

According to the above configuration, since the management control device is provided, it is possible to determine the priority of inputting the manipulating input signal among the plurality of slave robots that are in the standby state of the manipulating input signal inputted through the master device. Further, since the output device is provided, the information related to the priority determined by the management control device can be outputted so as to inform the operator of the robot system.

Thus, in a case where the input of the manipulating input signal is requested from the plurality of slave robots, the operator is able to easily determine to which slave robot the manipulating input signal should be first transmitted.

Therefore, the robot system according to the present disclosure has an effect that the operator is able to efficiently transmit the manipulating input signal to the plurality of slave robots through the master device.

According to the above configuration, the robot system according to the aspect of the present disclosure may further include a situation information acquisition part configured to acquire situation information indicative of a situation of the slave robot in a workspace, respectively. The management control device may determine the priority of transmitting the manipulating input signal based on the situation information of the slave robots acquired by the situation information acquisition part.

With the above configuration of the robot system according to the aspect of the present disclosure, the situation information acquisition part may acquire a lapsed time of a work being carried out by the slave robot as the situation information. The management control device may calculate a delay time of the work of the slave robot at the present time point based on a lapsed time of the work acquired by the situation information acquisition part, and according to the delay time, determine the priority of transmitting the manipulating input signal.

According to the above configuration, with the robot system according to the aspect of the present disclosure, the operator is able to transmit the manipulating input signal by giving the priority to the slave robot with a long delay of the work.

With the above configuration of the robot system according to the aspect of the present disclosure, the situation information acquisition part may acquire, as the situation information, at least one of information indicative of a position and a posture of the slave robot in the workspace. The management control device may determine whether the slave robot is in an abnormal state based on the at least one of information indicative of the position and the posture of the slave robot acquired by the situation information acquisition part, and according to the determination, determine the priority of transmitting the manipulating input signal.

According to the above configuration, with the robot system according to the aspect of the present disclosure, the operator is able to transmit the manipulating input signal by giving the priority to the slave robot in the abnormal state.

Effect of the Disclosure

The present disclosure is configured as described above, and has an effect that the operator is able to efficiently transmit the manipulating input signal to the plurality of slave robots through the master device.

BRIEF DESCRIPTION OF DRAWINGS

FIG. 3 is a view illustrating one example of operation sequences of a robot system according to Example 1 of Embodiment 1 of the present disclosure.

MODES FOR CARRYING OUT THE DISCLOSURE

Outline of the Present Disclosure

Figure 1:
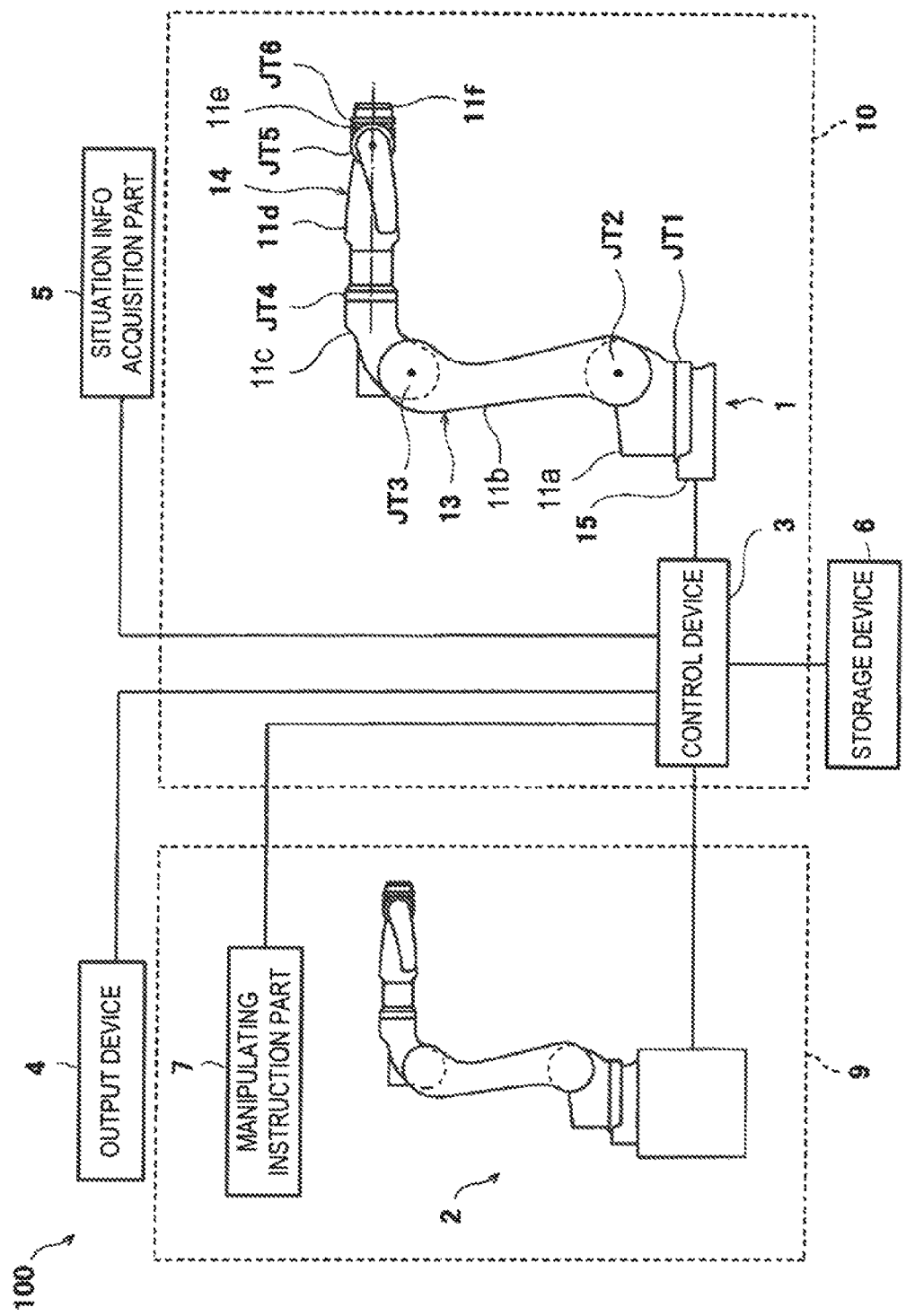
FIG. 1 is a schematic diagram illustrating one example of a configuration of a robot system according to Embodiment 1 of the present disclosure.

The present inventors have diligently studied about a system which is capable of achieving a collaborated work of a human and a robot. Especially, they have examined a system which is capable of achieving the collaborated work of the human and the robot by utilizing a robot system using a master-slave type robot which is comprised of a master device provided with a master arm and a slave robot provided with a slave arm.

First, a work comprised of a series of processes can be carried out by the robot system utilizing the master-slave type robot. Especially, it may be thought that the slave arm is operated in a manual mode according to manipulating instructions from an operator inputted through the master device in a process among the work, which requires an advanced sensor recognition technology etc., while the slave arm is operated in an automatic mode in other processes.

Meanwhile, in a case where the slave arm is operated in the automatic mode for a process comprised of a plurality of steps, they have noticed that, after the slave arm is operated in the automatic mode up to a given step, there may be a case where a determination of whether the automatic mode is continued as it is, or a change of the operating mode is required is necessary.

Thus, the present inventors have diligently repeated examinations, and acquired the following knowledge. That is, when the slave arm carries out the process comprised of the plurality of steps in the automatic mode, the control device which controls operation of the slave arm is configured to stop the operation of the slave arm in the automatic mode at the given steps, and further become in a standby state of a manipulating input signal transmitted from the master device. Then, the control device is configured, when the manipulating input signal is received, to determine whether the automatic mode is to be continued based on the manipulating input signal. Moreover, the control device is configured, when it determines that the automatic mode is not to be continued, to stand by a signal indicative of a switching instruction of the operating mode transmitted from the master device.

Thus, during the operation of the slave arm in the automatic mode, it is determined whether the automatic mode is to be continued, and when it is determined that the automatic mode is to be further continued, a suitable operating mode can be inquired to the operator.

Moreover, they have found out that the following problems arise in the robot manual feed control device disclosed in Patent Document 1 when it is configured to be provided with a plurality of slave robots, each having a slave arm and a control device. For example, in order for each of the plurality of slave robots to determine whether the automatic mode is to be continued, it is assumed that it is in the standby state of the manipulating input signal from the operator. In this case, they have found out that the operator may not be able to determine to which slave robot among the plurality of slave robots the manipulating input signal should be first transmitted. In such a case, it is configured to present the operator with a priority indicative of which slave robot should give a priority of transmitting the manipulating input signal. Thus, the operator is able to easily deter which slave robot among the slave robots in the standby state of the manipulating input signal should give the priority of transmitting the manipulating input signal.

Below, embodiments of the present disclosure will be described with reference to the accompanying drawings. Note that, below, the same reference characters are assigned to the same or corresponding components throughout the figures to omit redundant description.

Embodiment 1

First, a robot system 100 according to Embodiment 1 of the present disclosure is described with reference to FIG. 1. FIG. 1 is a schematic diagram illustrating one example of a configuration of the robot system 100 according to Embodiment 1 of the present disclosure.

The robot system 100 according to Embodiment 1 of the present disclosure is a system utilizing a master-slave type robot. That is, in the robot system 100, the operator who is located at a position distant from a workspace (outside of the workspace) moves, for example, a master arm 2 provided to a master device 9, a slave arm 1 installed in the workspace capable of operating so as to follow the motion of the master arm 2 to perform a specific work. Further, in the robot system 100, the slave arm 1 is also capable of automatically performing a given work without the intervention of the manipulation of the master arm 2 by the operator.

An operating mode in which the slave arm 1 is operated according to a manipulating instruction (instruction) inputted through the master arm 2 is herein referred to as the "manual mode." Note that "the manual mode" described above also includes a case where part of the operation of the slave arm 1 under automatic operation is corrected based on the manipulating instruction (instruction) inputted by the operator manipulating the master arm 2. For example, the case to be corrected may include the following operation. That is, the motion of the slave arm 1 may vibrate due to the operator's shaking etc. while the manual mode is set. In such a case, there may be a case where the motion of the slave arm 1 is automatically corrected so as to prevent the vibration from occurring.

Moreover, an operating mode in which the slave arm 1 is automatically operated according to a preset task program is herein referred to as the "automatic mode."

Further, the robot system 100 of Embodiment 1 is configured so that, when the slave arm 1 is operating in the automatic mode, the manipulating instruction (instruction) inputted through the master arm 2 is able to be reflected in the operation of the slave arm 1 to correct operation to be performed automatically. An operating mode in which the slave arm 1 is operated according to the preset task program in the state where a correcting instruction (instruction) inputted through the master arm 2 is able to be reflected is herein referred to as the "correctable automatic mode." Note that "the automatic mode" is distinguished from "the correctable automatic mode" in that the manipulation of the master arm 2 is not reflected in the operation of the slave arm 1 when the operating mode in which the slave arm 1 is operated is the automatic mode.

Configuration of Robot System According to Embodiment 1

As illustrated in FIG. 1, the robot system 100 is comprised of a slave robot 10, the master device 9, an output device 4, a situation information acquisition part 5, and a storage device 6. Note that, although not illustrated in particular in FIG. 1, the robot system 100 further includes a monitoring display device for the operator to check a work situation of the slave arm 1, and a monitoring camera which images the work situation of the slave arm 1. Note that the monitoring display device is installed in a space where the master device 9 is provided, the monitoring camera is installed in a space where the slave arm 1 is provided, and both are connected wiredly or wirelessly.

Configuration of Slave Robot

The slave robot 10 includes the slave arm 1, an end effector (not illustrated) attached to a tip end of the slave arm 1, and a control device 3 which governs the operations of the slave arm 1 and the end effector.

Slave Arm

The slave arm 1 performs, in a process containing a plurality of steps, processing the steps. That is, a certain work is comprised of a plurality of processes to which the operating mode of the slave arm 1 is set, respectively, and each process contains a plurality of steps. The slave arm 1 carries out the process of the step in the set operating mode.

The slave arm 1 includes a pedestal 15, an arm part 13 supported by the pedestal 15, and a wrist part 14 which is supported by a tip end of the arm part 11 and to which the end effector is attached. As illustrated in FIG. 1, the slave arm 1 is an articulated robot arm having a plurality of (three or more) joints JT1-JT6, and is constructed by serially coupling a plurality of links 11a-11f. In more detail, at the first joint JT1, the pedestal 15 and a base-end part of the first link 11a are coupled to each other so as to be rotatable about an axis extending vertically. At the second joint JT2, a tip-end part of the first link 11a and a base-end part of the second link 11b are coupled to each other so as to be rotatable about an axis extending horizontally. At the third joint JT3, a tip-end part of the second link 11b and a base-end part of the third link 11c are coupled to each other so as to be rotatable about an axis extending horizontally. At the fourth joint JT4, a tip-end part of the third link 11c and a base-end part of the fourth link 11d are coupled to each other so as to be rotatable about an axis extending in the longitudinal directions of the fourth link 11d. At the fifth joint JT5, a tip-end part of the fourth link 11d and a base-end part of the fifth link 11e are coupled to each other so as to be rotatable about an axis perpendicular to the longitudinal directions of the link 11d. At the sixth joint JT6, a tip-end part of the fifth link 11e and a base-end part of the sixth link 11f are twistably and rotatably coupled to each other. A mechanical interface is provided to a tip-end part of the sixth link 11f. The end effector corresponding to the contents of work is attached to the mechanical interface attachably and detachably.

The arm part 13 of the slave arm 1 is formed by a coupled body of the links and the joints, which is comprised of the first joint JT1, the first link 11a, the second joint JT2, the second link 11b, the third joint JT3, and the third link 11c, described above. Moreover, the wrist part 14 of the slave arm 1 is formed by a coupled body of the links and the joints, which is comprised of the fourth joint JT4, the fourth link 11d, the fifth joint JT5, the fifth link 11e, the sixth joint JT6, and the sixth link 11f, described above.

The joints JT1-JT6 are provided with drive motors M1-M6, respectively, as one example of an actuator which relatively rotates two members connected by the joint. The drive motors M1-M6 are, for example, servo motors which are servo-controlled by the control device 3. Moreover, the joints JT1-JT6 are provided with rotation sensors E1-E6 which detect rotational positions of the drive motors M1-M6, and current sensors C1-C6 which detect current for controlling the rotations of the drive motors M1-M6, respectively. The rotation sensors E1-E6 are, for example, encoders. Note that, in the description of the drive motors M1-M6, the rotation sensors E1-E6, and the current sensors C1-C6, 1-6 of the suffixes are given to the alphabet corresponding to the respective joints JT1-JT6. Below, when an arbitrary joint is illustrated among the joints JT1-JT6, the suffix is omitted and it is referred to as "JT," and the same is applied to drive motor M, the rotation sensor E, and the current sensor C.

Note that the configuration of the slave arm 1 described above is one example. The configuration of the slave arm 1 is not limited to this configuration, and the configuration may suitably be changed according to the contents of work which is carried out using the slave arm 1, the workspace, etc.

Control Device

Figure 2:
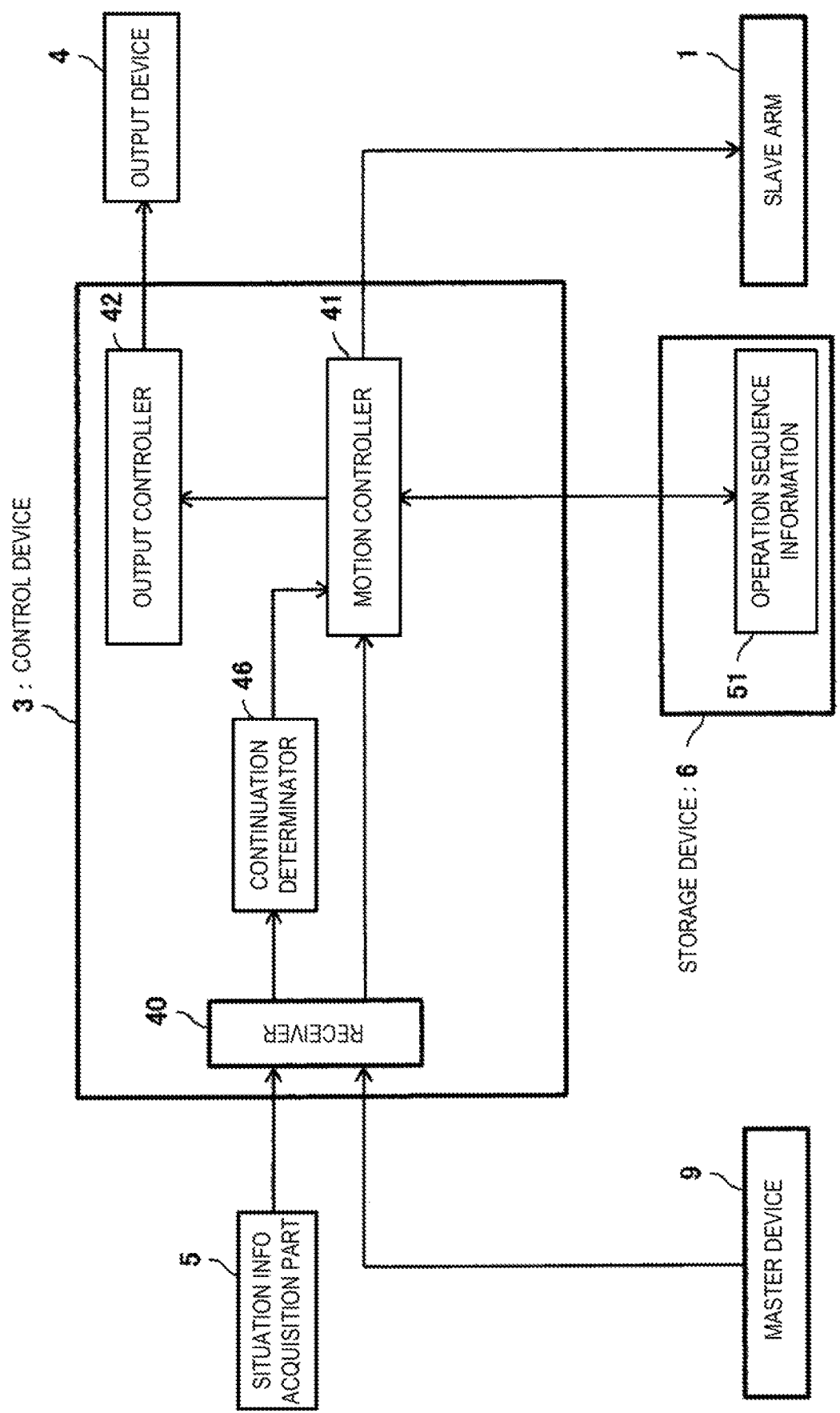
FIG. 2 is a block diagram illustrating one example of a functional structure according to a control device provided to the robot system illustrated in FIG. 1.

Next, the control device 3 which controls the operation of the slave arm 1 having the above configuration is described with reference to FIG. 2. FIG. 2 is a block diagram illustrating one example of a functional structure according to the control device 3 provided to the robot system 100 illustrated in FIG. 1.

The control device 3 is to control the operation of the slave arm 1, and as illustrated in FIG. 2, it includes a receiver 40, a motion controller 41, an output controller 42, and a continuation determinator 46, as functional blocks. The control device 3 may be comprised of, for example, an arithmetic part (not illustrated) comprised of a microcontroller, an MPU, a PLC (Programmable Logic Controller), a logic circuit, etc., and a memory part (not illustrated) comprised of a ROM, a RAM, etc. Moreover, each functional block provided to the control device 3 may be implemented by the arithmetic part of the control device 3 reading and executing a control program stored in the memory part.

The receiver 40 receives an input signal transmitted from the outside of the control device 3. The input signal received by the receiver 40 may be, for example, a signal transmitted from the master device 9, or a signal transmitted from the situation information acquisition part 5.

The motion controller 41 determines whether the operating mode of the slave arm 1 is to be the automatic mode based on operation sequence information 51, or whether it is to be the manual mode in which the slave arm 1 is operated based on the instructions inputted through the master arm 2 of the master device 9, or it is to be the correctable automatic mode in which the operation of the slave arm under operation in the automatic mode is corrected based on the instructions inputted through the master arm 2 of the master device 9. Then, the operation of the slave arm 1 is controlled according to the determined operating mode.

For example, when the receiver 40 receives the manipulating instruction (manipulating input signal) for a subsequent process from the master device 9 as the input signal, the motion controller 41 may determine the operating mode for the subsequent process which the slave arm 1 carries out by using the manipulating instruction (manipulating input signal) as a trigger. Alternatively, when a switching of the operating mode is set automatically, the motion controller 41 may determine the operating mode of the slave arm 1 in the subsequent process with reference to the operation sequence information 51 stored in the storage device 6.

When the operating mode is determined, the motion controller 41 controls the slave arm 1 to operate it in the determined operating mode. When determined that the slave arm 1 is to be operated in the automatic mode, the motion controller 41 reads the operation sequence information 51, and controls the slave arm 1 to carry out the operation defined in the operation sequence information 51. On the other hand, when determined that the slave arm 1 is to be operated in the manual mode, the motion controller 41 controls the slave arm 1 to operate based on the manipulating instruction (manipulating input signal) which the receiver 40 received from the master arm 2. Moreover, when determined that the slave arm 1 is to perform the correctable automatic operation, the motion controller 41 controls the slave arm 1 so that the operation in the automatic mode of the slave arm 1 becomes operation which is corrected based on the manipulating instruction (instruction) inputted through the master arm 2.

Note that the motion controller 41 may be configured, when operating the slave arm 1 in the automatic mode, to transmit information indicative of a termination of the automatic mode to the output controller 42 at the time of the end of the operation in the automatic mode.

The output controller 42 controls the output device 4 to output the information to be notified to the operator etc. For example, when the information indicative of the termination of the automatic mode is received from the motion controller 41, the output controller 42 controls the output device 4 to output the information. The output device 4 may be configured to output the notice of the termination of the automatic mode of the slave arm 1 by displaying it or expressing it by sound or light, according to the control instruction from the output controller 42. If configured in this way, the operator is able to grasp the end of the operation of the slave arm 1 in the automatic mode.

Further, the output controller 42 may be configured, when situation information is received from the situation information acquisition part 5, to control the output device 4 to output the situation information. In the case where it is configured in this way and when the output device 4 is the display device, the output device 4 is capable of displaying the operating situation etc. of the slave arm 1. Thus, the operator is able to monitor the operating situation etc. of the slave arm 1.

Situation Information Acquisition Part

The situation information acquisition part 5 acquires the situation information indicative of the situation of the slave arm 1 in the workspace. The situation information includes information utilized in order to recognize the position and/or posture of the slave arm 1 in the workspace, or the situation around the slave arm 1. More specifically, the situation information includes, for example, information required in order to enable the recognition of the situation of the slave arm 1 in the workspace and the situation around the slave arm 1, such as the position or posture of the slave arm 1 in the workspace, a spatial relationship between the slave arm 1 and the workpiece, or a spatial relationship between the slave arm 1 and the assembled component to which the workpiece is attached. The situation information acquisition part 5 is implementable with, for example, a sensor, an imaging device, a communication device, an encoder, etc. The sensor may include, for example, a laser sensor, a radar sensor or the like which measures a distance or a position to the workpiece (assembling component) or the assembled component. Further, it may include a stereoscopic camera which is a sensor for measuring a distance from the slave arm 1 to an object around thereof by using image data obtained from a plurality of imaging devices. The communication device may include, for example, a communication device which acquires information from the workpiece (assembling component) or the assembled component, or a sensor and an imaging device which are installed at given positions in the workspace. The encoder may include, for example, an encoder capable of detecting an amount of movement or the position of the slave arm.

Moreover, the situation information acquired by the situation information acquisition part 5 is not limited to the information utilized in order to recognize the position and/or posture of the slave arm 1 in the workspace, or the situation around the slave arm 1, which are described above.

For example, the situation information acquired by the situation information acquisition part 5 may be, for example, information indicative of a lapsed time of the work currently performed by the slave arm 1. If the situation information is information indicative of the lapsed time of the work currently performed by the slave arm 1, the situation information acquisition part 5 may be a measuring device which measures a duration of time which the slave arm 1 takes for processing a given step.

The situation information acquisition part 5 acquires situation information as required, and the acquired situation information is inputted into the control device 3 where it is used for the motion control of the slave arm 1. Further, the control device 3 may also be configured to control the output device 4 to output the situation information. The situation information acquisition part 5 may be attached to the slave arm 1 itself, or may be attached to a suitable position in the workspace. Moreover, the number of situation information acquisition parts 5 attached may be one, or may be plural. The attaching position and the attaching number are arbitrary, as long as a suitable number of situation information acquisition parts 5 are attached to a position where the situation information is able to be acquired appropriately.

Output Device

The output device 4 is to output the information transmitted from the control device 3, and for example, it is implementable by a display device, a speaker, a light source, a printer, a vibration generating device, etc. For example, if the output device 4 is the display device, the output device 4 displays the information transmitted from the control device 3. For example, if the output device 4 is the speaker, the output device 4 outputs the information transmitted from the control device 3 as sound. If the output device 4 is the light source, the output device 4 outputs the information transmitted from the control device 3 as light. If the output device 4 is the printer, the output device 4 prints out the information transmitted from the control device 3. If the output device 4 is the vibration generating device, the output device 4 outputs the information transmitted from the control device 3 as vibration. The output device 4 is provided at a suitable position where the operator of the master device 9 is able to sense the outputted information.

Storage Device

The storage device 6 is a readable and writable recording medium, and stores the operation sequence information 51 on the robot system 100. The operation sequence information 51 is a task program which defines the operation of the slave arm 1, and includes information related to the operation sequence defining the processing of each step which is carried out by the slave arm 1 in the workspace. In the robot system 100 according to this embodiment, specifically, it is information where the operation order, the operating mode of the slave arm 1, and the operation flow of each process are associated with each other, as illustrated in FIG. 3. FIG. 3 is a view illustrating one example of the operation sequence of the robot system 100 according to Example 1 of Embodiment 1 of the present disclosure.

Moreover, the storage device 6 may store scheduled route information (not illustrated) indicative of a planned route range of the slave arm 1. Note that the scheduled route information may include, for example, time series information of the planned position, posture and the like of the slave arm 1 when carrying out each process of the series of works. Thus, when it is configured that the storage device 6 stores the scheduled route information, the information can be utilized in order to detect whether the slave arm 1 is in a state where the slave arm 1 is deviated from the planned route range.

Note that, in the robot system 100 according to Embodiment 1, although the storage device 6 is provided separately from the control device 3, it may be provided integrally with the control device 3.

Master Device

The master device 9 is an input device which is installed outside the workspace and receives the manipulating instruction from the operator, and includes the master arm 2 and a manipulating instruction part 7.

In the robot system 100, when the operator moves the master arm 2, the slave arm 1 moves so as to follow the motion of the master arm 2. Since the master arm 2 has a similarity structure to the slave arm 1, description about the structure of the master arm 2 is omitted. Note that the master arm 2 may be, for example, an input device in which a directional input by a lever is possible (joystick), which has a non-similarity structure to the slave arm 1.

As the operator moves the master arm 2, manual operation information is generated and it is sent to the control device 3. In the robot system 100 according to Embodiment 1, when the operating mode in which the slave arm 1 is operated is the manual mode, the manipulating input signal is sent from the master arm to the control device 3, and the slave arm 1 moves so as to follow the motion of the master arm 2 according to the control instruction from the control device 3 based on the manipulating input signal. Moreover, for example, when the operating mode in which the slave arm 1 is operated is the correctable automatic mode, the manipulating input signal is sent from the master arm 2 to the control device 3, and the operation of the slave arm 1 under the automatic operation according to the control instruction from the control device 3 is corrected based on the manipulating input signal.

The manipulating instruction part 7 is an input device, which is installed outside the workspace similar to the master arm 2, receives an input from the operator, and transmits the received input to the control device 3 of the slave arm 1 as the manipulating input signal. The manipulating instruction part 7 may include an input switch for receiving the operator's input, or a mobile terminal, such as a tablet computer.

Note that the manipulating input signal transmitted to the control device 3 of the slave arm 1 from the master device 9 includes the signal inputted by the operator through the master arm 2 and the signal inputted by the operator through the manipulating instruction part 7.

Operation Sequence of Robot System

Next, the operation sequence of the work comprised of the series of processes carried out by the robot system 100 provided with the above configuration will be described by the following Examples 1 and 2.

Example 1

Figure 4:
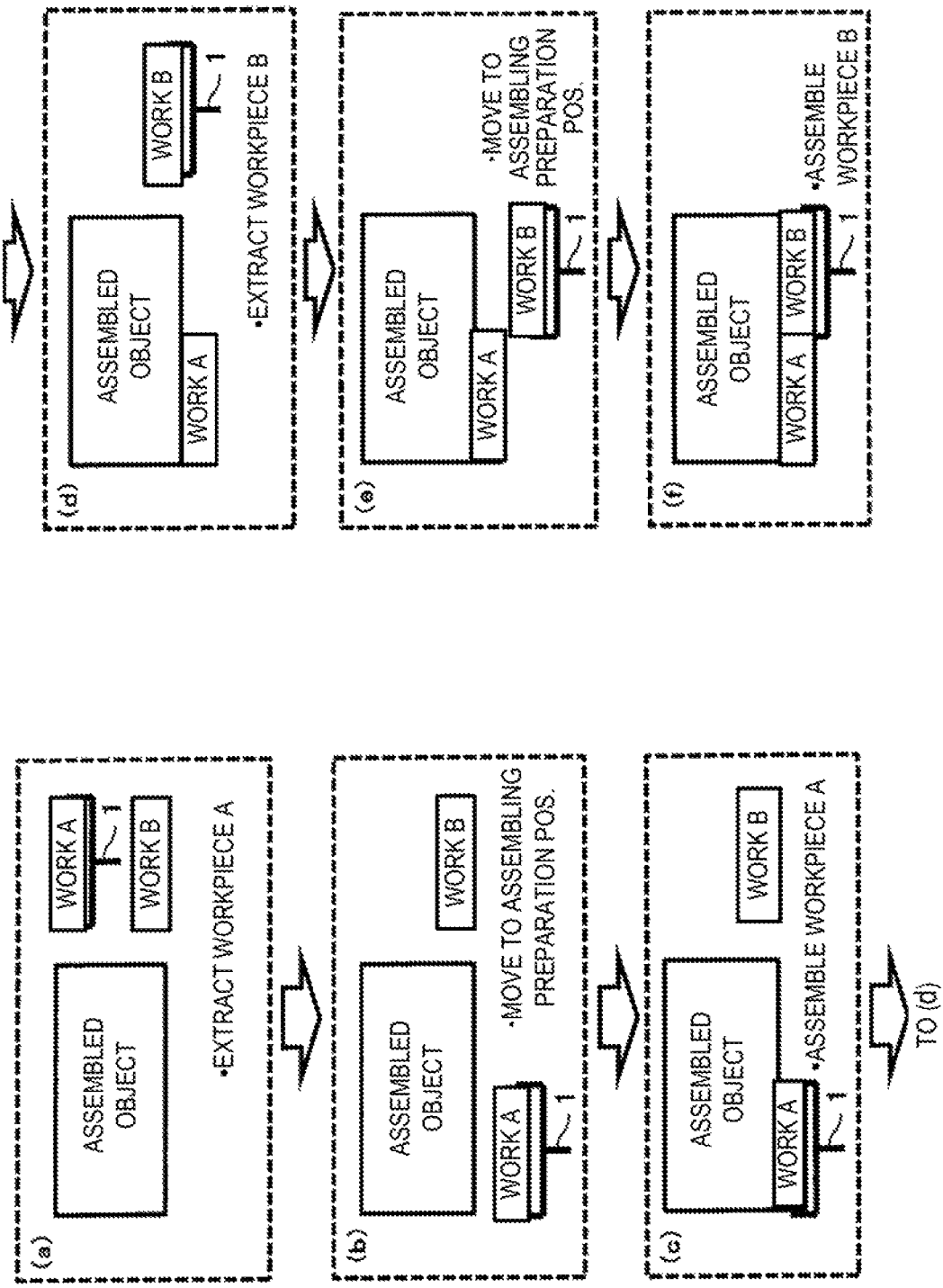
FIG. 4 is a view schematically illustrating one example of the slave arm which performs a work along the operation sequence illustrated in FIG. 3.
Figure 5:
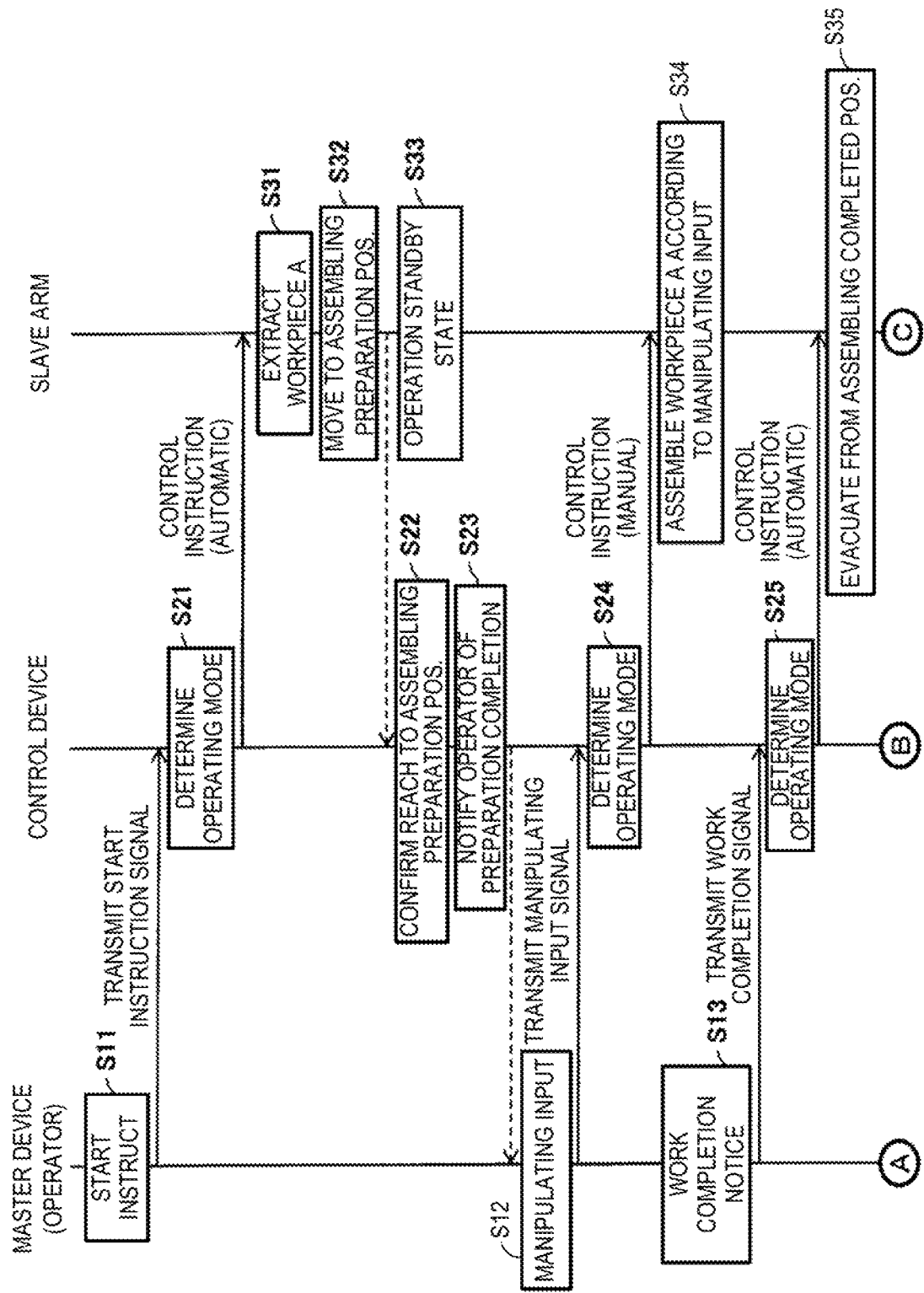
FIG. 5 is a flowchart illustrating one example of operation processings in the master device, the control device, and the slave arm, which carry out the operation sequences illustrated in FIG. 3.
Figure 6:
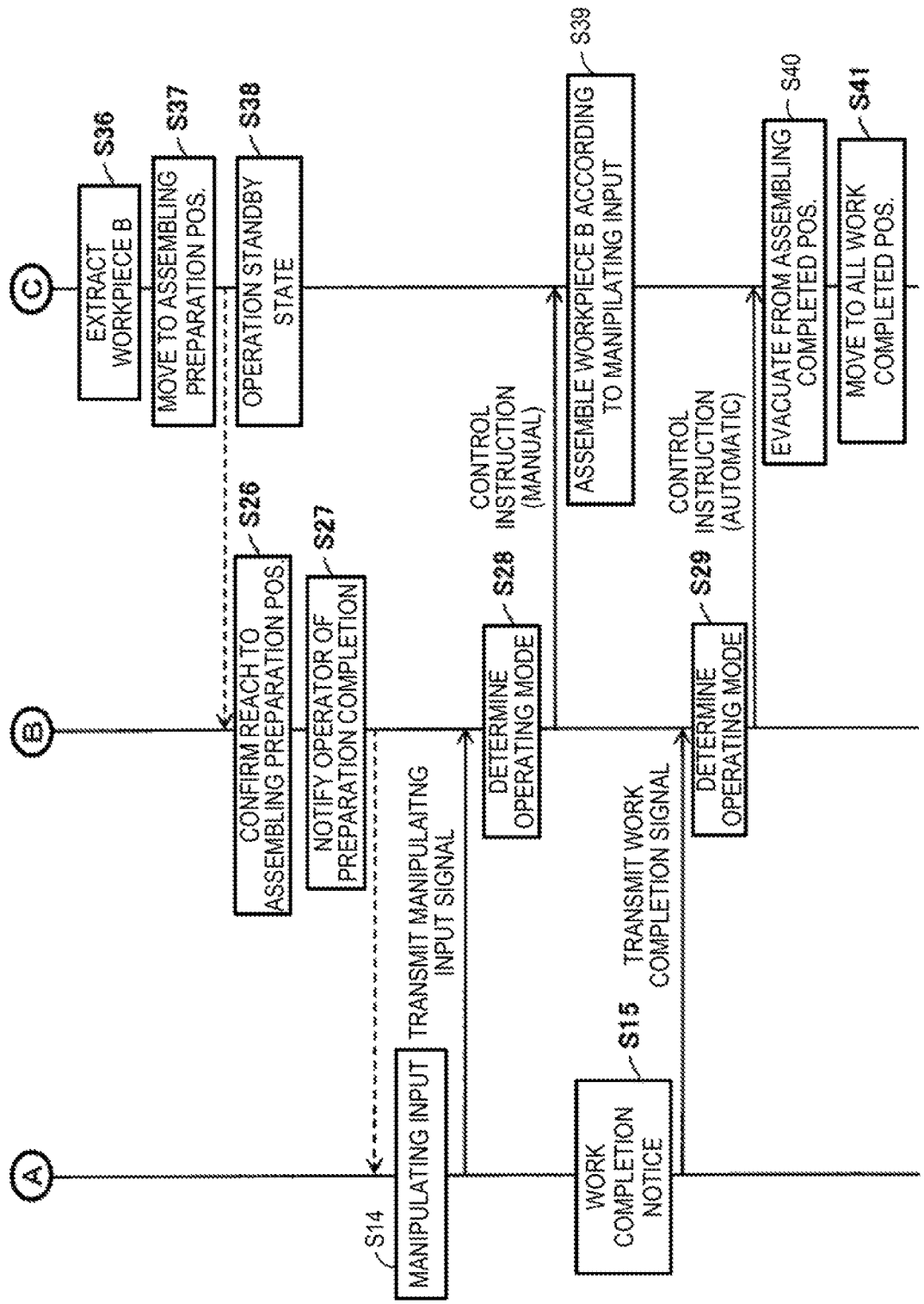
FIG. 6 is a flowchart illustrating the example of the operation processings in the master device, the control device, and the slave arm which carry out the operation sequences illustrated in FIG. 3.

In addition to FIG. 3 described above, with reference to FIGS. 4 to 6, the operation sequence of the robot system 100 according to Example 1 of Embodiment 1 of the present disclosure is described. FIG. 4 is a view schematically illustrating one example of the slave arm 1 which performs a work along the operation sequence illustrated in FIG. 3. FIGS. 5 and 6 are flowcharts illustrating one example of operation processings of the master device 9, the control device 3, and the slave arm 1 which carry out the operation sequence illustrated in FIG. 3, respectively.

In Example 1, the operation sequence of the robot system 100 is described using the assembling work of the workpiece to the assembled object as one example. The entire operation sequence illustrated in FIG. 3 is herein referred to as a "work," and each process illustrated by <1> to <5> in FIG. 3 as a "process." Moreover, the processing carried out at each process is referred to as a "step." In FIG. 3, <1> to <5> illustrates a performing order of each process in the work.

Note that the robot system 100 is configured so that the operation sequence information 51 is executed as the task program to operate the slave arm 1 along the operation sequence described above. In the operation sequence related to the work of Example 1, the slave arm 1 carries out in the automatic mode the movement from a position where the workpiece is stored to near a assembling position of the workpiece (assembling preparation position). Once the slave arm 1 brings the workpiece to the assembling preparation position, since positioning at the assembling position and the assembling work are complicated in the assembling of the workpiece to the assembled object, the slave arm 1 is designed so that the slave arm 1 carries out the positioning at the assembling position and the assembling work in the manual mode according to the manipulating instructions from the operator.

The operation sequence related to the work of Example 1 is applicable to a rigging process of an automobile where an automobile body is used as the assembled object, a front seat as the workpiece A, and a rear seat as the workpiece B. Alternatively, it is also applicable to an assembly process of a robot where an arm is used as the assembled object, a transmission as the workpiece A, and a motor as the workpiece B.

Note that, for convenience of explanation, although Examples 1 to 4 will be described below using the assembling work of the workpiece to the assembled object as one example, but the work performed using the robot system 100 is not limited to the assembling work. For example, it may be a paint work to the workpiece. The paint work may include, for example, a paint work in which the slave arm 1 paints the workpiece conveyed by a conveyor device (not illustrated) to a paint area (not illustrated). Alternatively, it may include a paint work in which the slave arm 1 paints while moving, in order to paint a main body of a large-sized device, such as a passenger airplane.

First, as illustrated in FIG. 5, the operator operates the manipulating instruction part 7 of the master device 9 to input a start instruction (Step S11). In response to the input of the start instruction, a start instruction signal which instructs a start of the operation sequence is transmitted from the master device 9 to the control device 3. In the control device 3, the receiver 40 is in the standby state of the manipulating input signal (start instruction signal), and when the receiver 40 receives the start instruction signal, the motion controller 41 determines the operating mode of the slave arm 1 (Step S21). The motion controller 41 may be configured to perform the determination of the operating mode of the slave arm 1 with reference to the operation sequence information 51 stored in the storage device 6. Alternatively, the motion controller 41 may be configured so that the information related to the operating mode of the slave arm 1 for the subsequent step is included in the start instruction signal transmitted from the master device 9, and the motion controller 41 performs based on this information.

When determining the operating mode based on the operation sequence information 51 illustrated in FIG. 3, the motion controller 41 determines the operating mode as follows. That is, as for the operation sequence information 51, the operating mode of the slave arm 1 is set to the automatic mode in the operation order <1> which is the first process. Therefore, the motion controller 41 determines that the operating mode of the slave arm 1 is the automatic mode, and controls the slave arm 1 to operate in the automatic mode. That is, with reference to the operation sequence information 51, the motion controller 41 transmits a control instruction to the slave arm 1 so that the slave arm 1 carries out each step of the operation order <1>.

Specifically, according to the control instruction (automatic mode) from the motion controller 41, the slave arm 1 moves to an extraction position of the workpiece A, and extracts the workpiece A (Step S31). Here, a spatial relationship between the workpiece A, the assembled object, and the slave arm 1 is in a state illustrated in (a) of FIG. 4. Once the workpiece A is extracted, the slave arm 1 moves to the assembling preparation position while holding the workpiece A, as illustrated in (b) of FIG. 4 (Step S32). Once the slave arm 1 moves to the assembling preparation position, it becomes in the standby state (operation standby state) of the manipulating instruction signal (Step S33).

Note that, the motion controller 41 is capable of determining whether the slave arm 1 reaches the assembling preparation position based on the situation information acquired from the situation information acquisition part 5. In FIG. 5, a dashed-line arrow extending toward before Step S22 of the control device 3 from after Step S32 of the slave arm 1 represents an acquisition of the situation information by the control device 3.

Then, if the motion controller 41 confirms that the slave arm 1 reaches the assembling preparation position (Step S22), it instructs to the output controller 42 so as to notify the operator of the completion of the preparation of the assembling work. The output controller 42 controls the output device 4 according to the instruction from the motion controller 41 to output information indicative of the preparation completion of the assembling work (Step S23). Here, the receiver 40 is in the standby state of the manipulating input signal transmitted from the master device 9. Note that, in FIG. 5, a dashed-line arrow extending toward before Step S12 of the master device 9 from after Step S23 of the control device 3 represents a detection of the notice of the preparation completion by the operator.

When the preparation completion is notified in the output device 4, the operator inputs a switching instruction of the operating mode from the manipulating instruction part 7 of the master device 9, and then performs an manipulating input using the master arm 2 of the master device 9 (Step S12). As a result of these inputs, an operating mode switching signal from the manipulating instruction part 7 and the manipulating input signal from the master arm 2 are transmitted to the control device 3, respectively. In the control device 3, when the receiver 40 receives the mode switching signal, the motion controller 41 determines the operating mode of the slave arm 1 (Step S24). Since the operating mode is the manual mode in the operation order <2> of the subsequent process, the motion controller 41 transmits to the slave arm 1 a control instruction based on the manipulating input signal inputted through the master arm 2. Thus, the slave arm 1 operates so as to follow the manipulation of the master arm 2. Specifically, the slave arm 1 carries out the assembling of the workpiece A to the assembled object as illustrated in (c) of FIG. 4 according to the manipulating input signal inputted through the master arm 2 (Step S34). Once the assembling of the workpiece A to the assembled object is completed, the operator operates the manipulating instruction part 7 of the master device 9 to input a work completion notice (Step S13). In response to the input of the work completion notice from the master device 9, a work completion signal is transmitted to the control device 3.

When the receiver 40 receives the work completion signal, in the control device 3, the motion controller 41 determines the operating mode of the slave arm 1 in the subsequent process (Step S25). The motion controller 41 may be configured to perform the determination of the operating mode of the slave arm 1 with reference to the operation sequence information 51 stored in the storage device 6. Alternatively, the motion controller 41 may be configured so that, the information related to the operating mode of the slave arm 1 for the subsequent step is included in the work completion signal transmitted from the master device 9, and the motion controller 41 performs based on this information.

In the example of the operation sequence information 51 illustrated in FIG. 3, the operating mode is set to the automatic mode in the operation order <3> of the subsequent process. Then, the motion controller 41 determines that the operating mode is the automatic mode, and with reference to the operation sequence information 51, it transmits a control instruction to the slave arm 1 so that the slave arm 1 carries out each step of the operation order <3>.

Specifically, according to the control instruction from the motion controller 41, the slave arm 1 is evacuated from an assembling completed position of the workpiece A (Step S35). Then, the slave arm 1 extracts the workpiece B, as illustrated in (d) of FIG. 4 (Step S36). Once the workpiece B is extracted, the slave arm 1 moves to the assembling preparation position while holding the workpiece B, as illustrated in (e) of FIG. 4 (Step S37). When the slave arm 1 moves to the assembling preparation position, it becomes in the standby state of the manipulating instruction signal (Step S38).

Note that the motion controller 41 may be configured to determine whether the slave arm 1 reaches the assembling preparation position based on the situation information acquired from the situation information acquisition part 5 similar to Step S32. In FIG. 6, a dashed-line arrow extending toward before Step S26 of the control device 3 from after Step S37 of the slave arm 1 represents an acquisition of the situation information by the control device 3.

Then, when the motion controller 41 confirms that the slave arm 1 reaches the assembling preparation position, it instructs the output controller 42 to notify the operator of the completion of the preparation of the assembling work (Step S26). The output controller 42 controls the output device 4 to output the information indicative of the preparation completion of the assembling work (Step S27). Then, the receiver 40 becomes in the standby state of the manipulating input signal transmitted from the master device 9. Note that, in FIG. 6, a dashed-line arrow extending toward before Step S14 of the master device 9 from after Step S27 of the control device 3 represents that the operator detects the notice of the preparation completion outputted from the output device 4.

When the assembling work preparation completion of the workpiece B is notified in the output device 4, the operator performs an manipulating input with a switching instruction of the operating mode by using the master arm 2 and the manipulating instruction part 7 of the master device 9 (Step S14). The switching instruction of the operating mode and the manipulating input inputted through the master device 9 are transmitted to the control device 3 as the operating mode switching signal and the manipulating input signal. In the control device 3, when the receiver 40 receives the operating mode switching signal and the manipulating input signal, the motion controller 41 determines the operating mode of the slave arm 1 in the subsequent process (Step S28). In the example of the operation sequence information 51 illustrated in FIG. 3, the operating mode is set to the manual mode in the following operation order <4>. Then, the motion controller 41 determines that the operating mode is the manual mode, and transmits to the slave arm 1 the control instruction (manual mode) based on the manipulating input signal received from the master arm 2. Thus, the slave arm 1 operates so as to follow the manipulation of the master arm 2. Specifically, the slave arm 1 carries out the assembling of the workpiece B to the assembled object, as illustrated in (f) of FIG. 4, according to the manipulating input from the master arm 2 (Step S39). Once the assembling of the workpiece B to the assembled object is completed, the operator operates the manipulating instruction part 7 of the master device 9 to input the work completion notice (Step S15). Then, the work completion notice inputted by the manipulating instruction part 7 is transmitted to the control device 3.

When the receiver 40 of the control device 3 receives the work completion signal, the motion controller 41 determines the operating mode of the slave arm 1 in the subsequent process (Step S29). In the example of the operation sequence information 51 illustrated in FIG. 3, the operating mode is set to the automatic mode in the operation order <5>. Then, the motion controller 41 determines that the operating mode is the automatic mode, and it controls the slave arm 1 so that the slave arm 1 automatically carries out each step of the operation order <5> which is the subsequent process.

Specifically, according to the control instruction (automatic mode) from the motion controller 41, the slave arm 1 is evacuated from the assembling completed position of the workpiece B (Step S40). Then, the slave arm 1 moves to an all work completed position (Step S41).

As described above, the robot system 100 according to Example 1 of Embodiment 1 of the present disclosure carries out the operation sequence related to the work comprised of the series of processes. Thus, in the work comprised of the series of processes, for example, the slave arm 1 is capable of carrying out rough operation in the automatic mode, and the slave arm 1 is capable of carrying out fine operation in the manual mode in which the slave arm 1 is operated according to the manipulating input from the operator.

As described above, the determination of the operating mode by the motion controller 41 may be carried out with reference to the operation sequence information 51 by using the reception by the receiver 40 of the start instruction signal, the manipulating input signal, or the work completion signal transmitted from the master device 9, as a trigger. Alternatively, the information indicative of the operating mode carried out in the subsequent process may be contained in the start instruction signal, the manipulating input signal, or the work completion signal, and the motion controller 41 may be configured to determine the operating mode based on the information indicative of the operating mode contained in the signal transmitted from the master device 9. If the motion controller 41 is configured to determine the operating mode based on the signal transmitted from the master device 9, it is not necessary to contain the information related to the operating mode in the operation sequence information 51 stored in the storage device 6.

Example 2

Continuation Permission Determination &
Operating Mode Determination

Moreover, Example 1 described above is configured, in the process where the motion controller 41 determines that the operating mode is the automatic mode, so that the slave arm 1 is operated in the automatic mode in all the steps contained in the process. However, it is not limited to this configuration, but even in the process determined to be the automatic mode, it may also be configured to determine whether a continuation of the operation of the slave arm 1 in the automatic mode is permitted according to the work situation etc. of the slave arm 1, and to be switchable of the operating mode from the automatic mode if needed.

For example, when the slave arm 1 evacuates from the assembling completed position in the automatic mode at Step S35 illustrated in FIG. 5 in Example 1, it may be configured so that the slave arm 1 does not successively perform the work at Step S36 illustrated in FIG. 6 in the automatic mode, but it is determined whether the work at Step S36 is to be continuously performed in the automatic mode. In other words, it may be configured so that the slave arm 1 operates in the automatic mode up to Step S35, and it is determined whether the automatic mode is to be continued for Step S36 and subsequent steps. Note that the timing of the permission determination of the continuation of the automatic mode is not limited to steps after Step S35. It is suitable for the timing of the permission determination of the continuation of the automatic mode to be at a position before carrying out a given step based on the contents of the step carried out by the slave arm 1.

Note that, if the work performed in Examples 1 and 2 is the paint work as described above, the process in which the slave arm 1 is scheduled to operate in the automatic mode may be, for example, a process in which the slave arm 1 is scheduled to paint the workpiece in the automatic mode. Moreover, in this process, the timing of the continuation permission determination of the automatic mode may be, for example, when the slave arm 1 has painted in the automatic mode up to a given position in a painting surface. In this case, the step to be determined the continuation permission of the automatic mode becomes a step of painting which is performed by the slave arm 1 to the painting surface after the given position.

Below, with reference to FIGS. 2 and 7, in the process where the slave arm 1 is scheduled to be operated in the automatic mode, a configuration in which the permission of the continuation of the automatic mode is determined when carrying out the steps after the given step contained in the process is described as Example 2.

Figure 7:
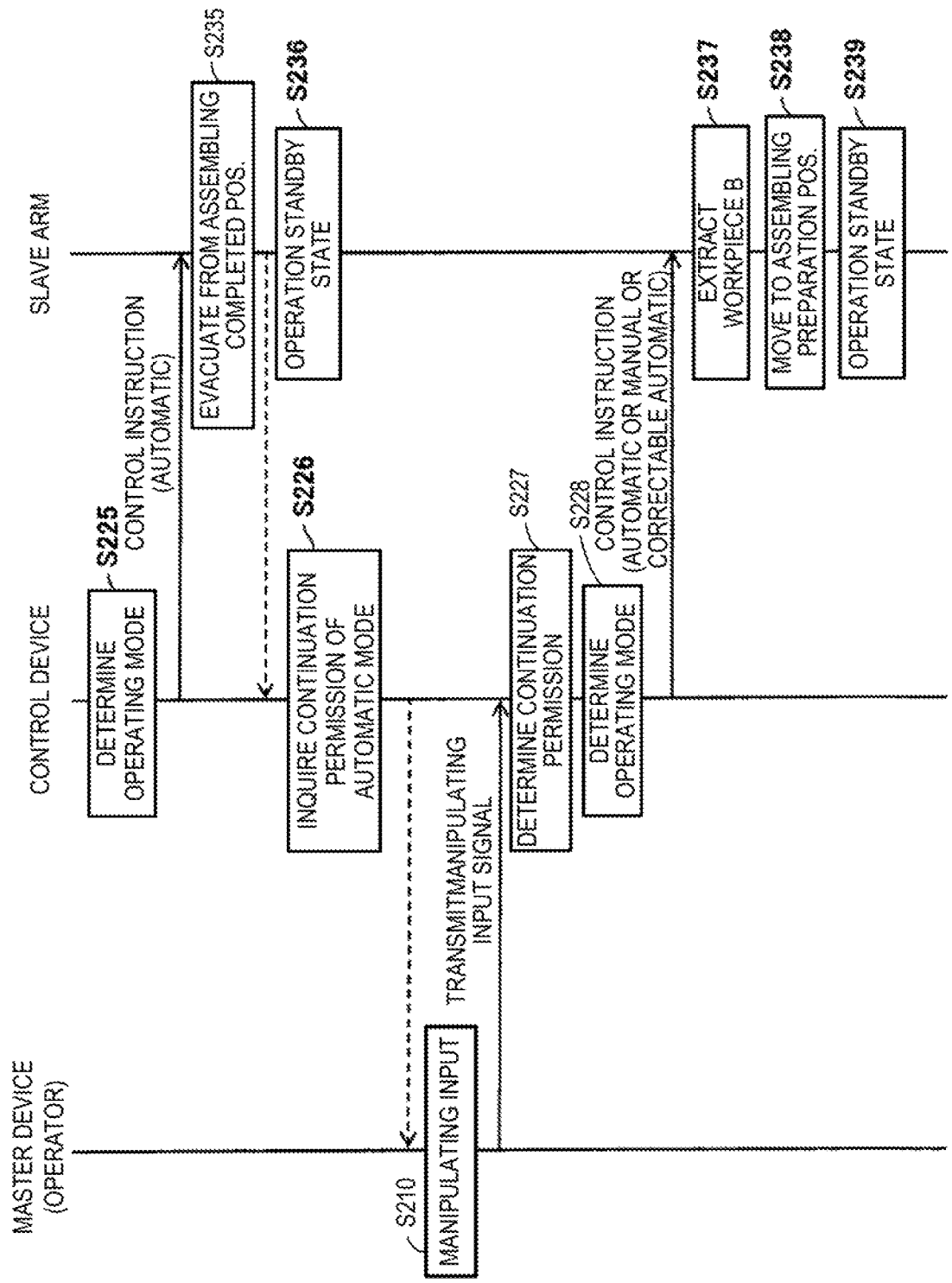
FIG. 7 is a flowchart illustrating one example of an operation sequence of a robot system according to Example 2 of Embodiment 1 of the present disclosure.

FIG. 7 is a flowchart illustrating one example of the operation sequence of the robot system according to Example 2 of Embodiment 1 of the present disclosure. In FIG. 7, the operation of the robot system according to Example 2 is described using a plurality of steps contained in the process of the operation order <3> illustrated in FIG. 3, as one example. Therefore, Steps S235, and S237 to S239 carried out by the slave arm 1 in FIG. 7 correspond to Steps S35-S38 carried out by the slave arm 1 in FIGS. 5 and 6. Moreover, Step S225 carried out by the control device 3 in FIG. 7 corresponds to Step S25 carried out by the control device 3 in FIG. 5. Thus, detailed description of these steps is omitted.

First, at Step S225, the motion controller 41 of the control device 3 determines the operating mode in the next process which is scheduled to be carried out by the slave arm 1. In the example of the operation sequence information 51 illustrated in FIG. 3, the operating mode is set to the automatic mode in the operation order <3> of the subsequent process. Then, the motion controller 41 determines that the operating mode is the automatic mode. Then, the motion controller 41 transmits the control instruction (automatic mode) to the slave arm 1 to control the slave arm 1 to carry out each step of the operation order <3> in the automatic mode. Then, in response to the control instruction from the motion controller 41, the slave arm 1 is automatically evacuated from the assembling completed position of the workpiece A (Step S235).

Next, the motion controller 41 detects that the slave arm 1 has evacuated from the assembling completed position and has moved to the given position based on the situation information acquired by the situation information acquisition part 5. After this detection, the motion controller 41 instructs the output controller 42 to inquire whether the continuation of the automatic mode is to be permitted. According to the instruction from the motion controller 41, the output controller 42 controls the output device 4 to output the inquiry of whether the continuation of the automatic mode is to be permitted (Step S226). Here, the motion controller 41 suspends the operation of the slave arm 1 in the automatic mode, and stands by as an operation standby state (Step S236). Moreover, the receiver 40 of the control device 3 is in a standby state of the manipulating input signal transmitted from the master device 9.

Note that, in FIG. 7, a dashed-line arrow extending toward before Step 226 of the control device 3 from after Step S235 of the slave arm 1 represents that the control device 3 receives the situation information utilized in order to check that the slave arm 1 has moved to the given position. Moreover, in FIG. 7, a dashed-line arrow extending toward before Step S210 of the master device 9 from after Step S226 of the control device 3 represents that the operator detects the inquiry of whether the continuation of the automatic mode is to be permitted.

Once the inquiry of whether the continuation of the automatic mode is to be permitted is notified by the output device 4, the operator operates the manipulating instruction part 7 of the master device 9 to input instruction information related to whether the continuation of the automatic mode is to be permitted (Step S210). Then, the instruction information inputted through the manipulating instruction part 7 is transmitted to the control device 3 as the manipulating input signal. In the control device 3, when the receiver 40 receives the manipulating input signal, the continuation determinator 46 determines whether the continuation of the operation of the slave arm 1 in the automatic mode is permitted (Step S227). Then, the continuation determinator 46 notifies a determination result to the motion controller 41. The motion controller 41 determines the operating mode of the slave arm 1 based on the determination result notified from the continuation determinator 46 (Step S228), and controls the slave arm 1 to operate in the determined operating mode. For example, if the determination result notified from the continuation determinator 46 is a permission of the continuation of the automatic mode, the motion controller 41 leaves the operating mode of the slave arm 1 as the automatic mode, and transmits a control instruction to the slave arm 1 to control the slave arm 1 to operate continuously in the automatic mode.

On the other hand, if the determination result notified from the continuation determinator 46 is not a permission of the continuation of the operation of the slave arm 1 in the automatic mode, the motion controller 41 determines that the operating mode of the slave arm 1 is the manual mode or the correctable automatic mode. Here, if the operating mode of the slave arm 1 is the manual mode, the motion controller 41 controls the slave arm 1 to operate in the manual mode according to the manipulating input signal from the master arm 2 received by the receiver 40. Alternatively, if the operating mode of the slave arm 1 is the correctable automatic mode, the motion controller 41 controls the slave arm 1 to operate so that part of the operation of the slave arm 1 in the automatic mode is corrected by the manipulating input signal from the master arm 2.

That is, when the determination result notified from the continuation determinator 46 is the permission of the continuation of the automatic mode, the slave arm 1 automatically extracts the workpiece B (Step S237), moves to the assembling preparation position (Step S238), and becomes in the operation standby state for the subsequent process (Step S239).

On the other hand, when the determination result notified from the continuation determinator 46 is not the permission of the continuation of the automatic mode, the slave arm 1, for example, extracts the workpiece B in the manual mode or the correctable automatic mode (Step S237), moves to the assembling preparation position (Step S238), and becomes in the operation standby state for the subsequent process (Step S239). Alternatively, when the determination result notified from the continuation determinator 46 is not the permission of the continuation of the operation of the slave arm 1 in the automatic mode, the slave arm 1 may not be carried out Steps S237-S239, and stay in a state where the operation is suspended.

Note that, although not illustrated in particular in FIG. 7, if the continuation determinator 46 determines that the continuation of the automatic mode is not permitted at Step S227, the motion controller 41 instructs the output controller 42 to inquire of the operating mode to be carried out at the next step and subsequent steps. Then, in response to the instruction, the output controller 42 may also be configured to control the output device 4 to output the inquiry of the operating mode. Moreover, the receiver 40 of the control device 3 may be configured, when the continuation determinator 46 determines the continuation of the automatic mode is not permitted, to become in an input standby state of the manipulating input signal containing the information, which specifies the operating mode, inputted through the master device 9.

In Example 2, although the configuration in which the operator is inquired of whether the continuation of the automatic mode is to be permitted, and the continuation determinator 46 determines whether the automatic mode is to be continued based on the manipulating input signal inputted through the manipulating instruction part 7 of the master device 9 is described, the present disclosure is not limited to this configuration. It may be configured so that the continuation determinator 46 determines whether the automatic mode is to be continued based on the situation information acquired by the situation information acquisition part 5, without inquiring the operator of whether the continuation of the automatic mode is to be permitted.

For example, the continuation determinator 46 may be configured to determine, according to the progress situation of each step in the process to be carried out by the slave arm 1, whether the continuation of the automatic mode is to be permitted, before carrying out a given step. More specifically, it is assumed that the robot system 100 includes, as the situation information acquisition part 5, a measuring part which measures a completion time of each step carried out by the slave arm 1. Before carrying out the given step (in the example of FIG. 7, the extraction of the workpiece B), the continuation determinator 46 compares the time at which a previous step of the step (in the example of FIG. 7, the evacuation from the assembling position) is completed, with a planned completion time of the previous step (a standard time required for processing the previous step), and if the time offset is more than a given range, it determines that the continuation of the automatic mode is not permitted. On the contrary, the completion time of the evacuation from the assembling position may be compared with the planned completion time of the evacuation from the assembling position (a standard time required for completing the evacuation), and if the time offset falls within the given range, the continuation determinator 46 may be configured to permit the continuation of the automatic mode. If configured in this way, Step S226 carried out by the control device 3 in FIG. 7, and Step S210 carried out by the master device 9 can be omitted. Note that details of the standard time will be described later.

Moreover, for example, if a sensor which grasps the position of the slave arm 1 in the workspace is provided as the situation information acquisition part 5, the continuation determinator 46 may be configured to determine whether the continuation of the automatic mode is to be permitted based on the result detected by the sensor. More specifically, based on the detection result of the sensor described above, it is determined at Step S235 whether the slave arm 1 is evacuated within a given range. Then, if it is determined that the slave arm 1 has not evacuated within the given range, the continuation determinator 46 does not permit the continuation of the automatic mode. On the other hand, if it is determined that the slave arm 1 exists within the given range, the continuation determinator 46 may be configured to permit the continuation of the automatic mode.

Embodiment 2

Configuration of Determining Priority to Transmit Manipulating Input Signals

In the robot system 100 according to Embodiment 1 and Examples 1 and 2 of Embodiment 1 described above, the configuration in which one slave robot 10 is provided in the workspace is described as the example. However, it may be configured to be provided with a plurality of slave robots 10 in the workspace. For example, in a production line etc., it is a case where the slave robot 10 is provided to each process, etc.

Figure 8:
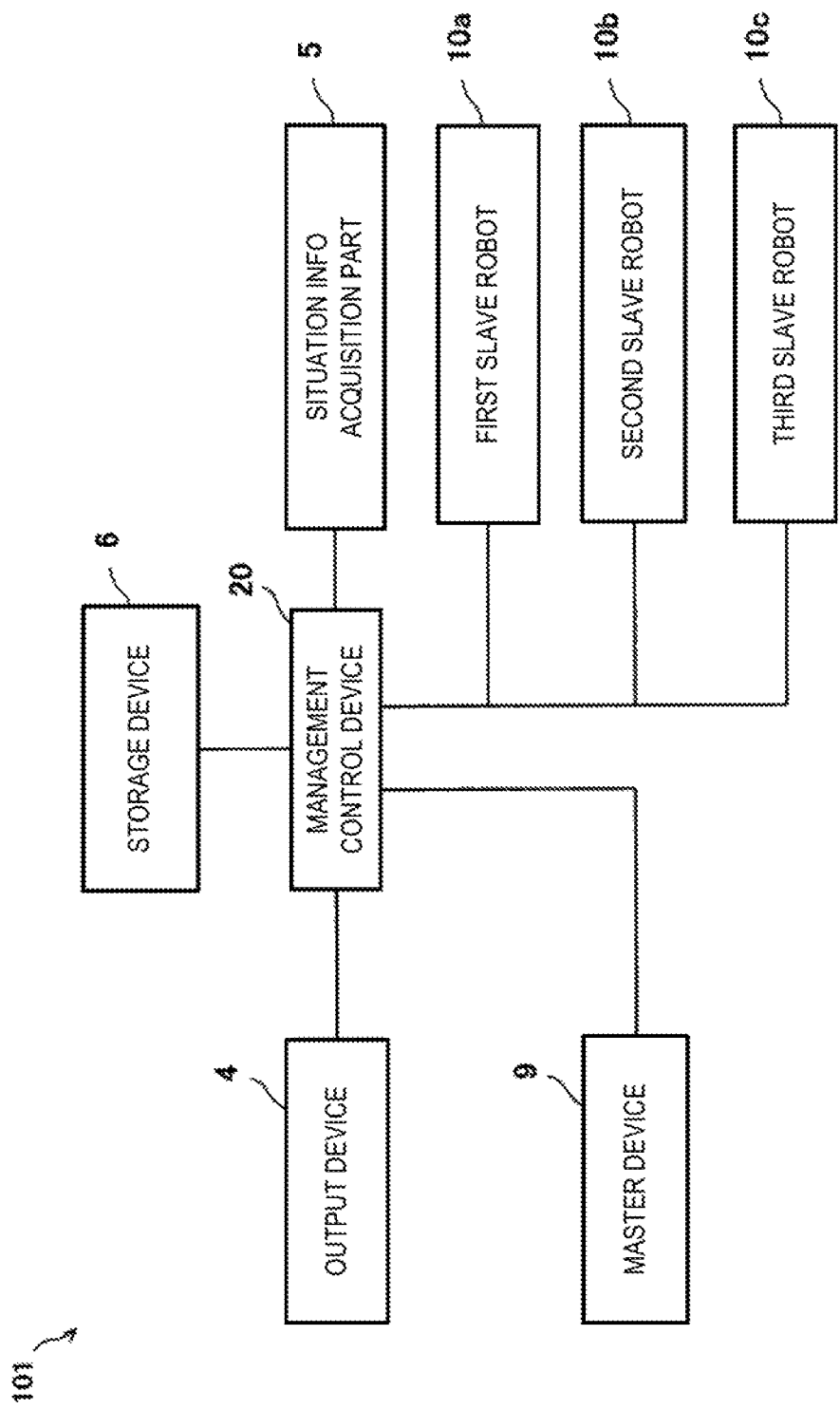
FIG. 8 is a block diagram illustrating one example of a functional structure of the robot system according to Embodiment 2.

Below, with reference to FIG. 8, a configuration in which, as a robot system 101 according to Embodiment 2, a plurality of slave robots (a first slave robot 10a, a second slave robot 10b, and a third slave robot 10c) are provided in the workspace, and the operator operates these first to third slave robots 10a-10c through the master device 9, is described. Note that, when the first slave robot 10a, the second slave robot 10b, and the third slave robot 10c do not need to be illustrated by particularly distinguishing from each other, it is simply referred to as the slave robot 10. FIG. 8 is a block diagram illustrating one example of a functional structure of the robot system 101 according to Embodiment 2.

As illustrated in FIG. 8, the robot system 101 according to Embodiment 2 differs as compared with the configuration of the robot system 100 according to Embodiment 1 illustrated in FIG. 1 in that it has a plurality of slave robots 10

(the first to third slave robots 10a-10c). Note that, since each of the first slave robot 10a, the second slave robot 10b, and the third slave robot 10c has the same configuration as the slave robot 10 according to Embodiment 1 illustrated in FIG. 1, description thereof is omitted.

Moreover, the robot system 101 according to Embodiment 2 is different from the robot system 100 according to Embodiment 1 in that it is provided with a management control device 20. Further, each of the first to third slave robots 10a-10c is also different in that the communication with the master device 9, the output device 4, the storage device 6, or the situation information acquisition part 5 is performed through the management control device 20. Since other configurations of the robot system 101 according to Embodiment 2 are similar to the configuration of the robot system 100 according to Embodiment 1, the same reference characters are given to similar components to omit description thereof.

Note that, as illustrated in FIG. 8, the robot system 101 is configured to be provided with the three slave robots 10, the number of slave robots 10 to be provided is not limited to three. Moreover, although the robot system 101 is configured to be provided with a single situation information acquisition part 5, but it is not limited to this configuration, and the situation information acquisition parts 5 may be provided corresponding to the first to third slave robots 10a-10c, respectively. That is, as long as the situation information acquisition part(s) 5 is capable of acquiring the situation information related to the respective first to third slave robots 10a-10c, the number to be provided may be suitably determined according to the kind etc. of information to be acquired as the situation information. Moreover, although the robot system 101 is configured so that a single output device 4 is provided at a suitable position where the operator of the master device 9 is able to detect information which is outputted, the number of output devices 4 provided is not limited to one. The output device 4 may be provided per kind of information to output, or may be provided for each of the first to third slave robots 10a-10c.

The management control device 20 manages the operations of the first to third slave robots 10a-10c. For example, when the situation information acquired by the situation information acquisition part 5 is information indicative of lapsed times of works which are carried out by the first to third slave robots 10a-10c, the management control device 20 is capable of managing progress situations of the works performed by the first to third slave robots 10a-10c based on the situation information, respectively. Alternatively, if it is configured so that, when each of the first to third slave robots 10a-10c completes a work at a given step, each notifies the completion to the management control device 20, the management control device 20 is also capable of managing the progress situation of the step carried out by each of the first to third slave robots 10a-10c based on the notice.

Alternatively, if the situation information acquired by the situation information acquisition part 5 is information indicative of the position of each of the first to third slave robots 10a-10c in the workspace, the management control device 20 is also capable of managing the current position of each of the first to third slave robots 10a-10c based on the situation information.

Further, if information indicative of the position and/or posture of each of the first to third slave robots 10a-10c in the workspace is acquired by the situation information acquisition part 5, the management control device 20 is also capable of determining based on the information whether each of the first to third slave robots 10a-10c is in an abnormal state, and managing the determination result. Note that details of a configuration related to the determination by the management control device 20 of whether it is in the abnormal state will be described later.

Moreover, the management control device 20 is to govern interfaces between the master device 9, the output device 4, the situation information acquisition part 5, the storage device 6, and the first to third slave robots 10a-10c. For example, the management control device 20 links the master device 9 to the slave robot 10 to be operated using the master device 9, and the manipulating input signal received from the master device 9 is transmitted to the slave robot 10 which is a link destination. Alternatively, the signal received from each of the first to third slave robots 10a-10c is transmitted to the output device 4 to control so as to output information based on the signal, or cause the output device 4 or each of the first to third slave robots 10a-10c to transmit the situation information acquired by the situation information acquisition part 5. Moreover, if the slave robot 10 reads the operation sequence information 51 stored in the storage device 6, the slave robot 10 may be configured to be capable of accessing the storage device 6 through the management control device 20.

Meanwhile, in the robot system 101 provided with the plurality of slave robots 10, there may be a case where the manipulating input from the operator through the master device 9 is requested from each of the plurality of slave robots 10. For example, as illustrated in Example 2, it may be a case where the continuation permission of the automatic mode is inquired to the operator from each of the first to third slave robots 10a-10c. In such a case, the operator cannot decide which slave robot 10 among the first to third slave robots 10a-10c should be given the priority to input of whether the automatic mode is to be continued.

Thus, in the robot system 101 according to Embodiment 2, when the continuation permission of the automatic mode is inquired to the operator from each of the first to third slave robots 10a-10c, the management control device 20 controls the output device 4 to output that there is an inquiry described above from each of the first to third slave robots 10a-10c. Further, the priority to transmit the manipulating input signal from the master device 9 is determined among the first to third slave robots 10a-10c which are in the standby state of the manipulating input signal, and the output device 4 is controlled to output the determined priority as well.

Note that, for example, the management control device 20 may determine the priority to transmit the manipulating input signal so that the priority is given to one among the first to third slave robots 10a-10c which takes a longer processing time to finish all the processes. If determining the priority in this way, the robot system 101 may be configured as follows. That is, a standard time which is a standard processing time required for carrying out each step in each process by each of the first to third slave robots 10a-10c is set beforehand, and information related to the standard time is stored in the storage device 6. Moreover, the situation information acquisition part 5 measures a lapsed time of the work which is carried out by each of the first to third slave robots 10a-10c.

The management control device 20 calculates a delay time from the standard time at the present time point of each the first to third slave robots 10a-10c which is in the standby state of the manipulating input signal, based on the information related to the standard time stored in the storage device 6 and the lapsed time of the work measured by the situation information acquisition part 5. Further, for a scheduled step to be carried out in future, the standard time of the step is calculated. Then, based on the delay time from the standard time at the present time point and the standard time which is estimated to be required for the scheduled step to be carried out in future, a processing time which is estimated to be finally required when each of the first to third slave robots 10a-10c carries out all the steps is calculated. Then, a higher priority is set to the slave robot 10 for a longer processing time for carrying out all the steps. Here, if the processing time required for carrying out all the steps is determined to be the same, it may be determined so that the slave robot 10 with a larger time delay from the standard time at the present time point is given a higher priority.

More specifically, when the continuation permission of the automatic mode is inquired and the first to third slave robots 10a-10c are in the standby state of the manipulating input signal for the inquiry, the management control device 20 is able to determine the priority as follows. That is, the management control device 20 acquires from the situation information acquisition part 5 an actual time which passed by the time each of the first to third slave robots 10a-10c reaches Step S236 illustrated in FIG. 7. Moreover, the management control device 20 acquires from the storage device 6 the information related to the standard time of a time which passed by the time each of the first to third slave robots 10a-10c reaches Step S236. Then, the management control device 20 compares the actual time acquired by the situation information acquisition part 5 with the standard time acquired from the storage device 6, and calculates a delay time from the standard time at the time point reaching Step S236 for each of the first to third slave robots 10a-10c. Further, a processing time (standard time) of a schedule step to be carried out in future at and after Step S236 is calculated, and based on the delay time and the processing time of the scheduled step to be carried out in future, the processing time estimated to be required for completing all the steps is calculated by each of the first to third slave robots 10a-10c, and the priority is determined so that a higher priority is given to those with a longer processing time.

Then, the management control device 20 causes the output device 4 to output the information related to the first to third slave robots 10a-10c in the standby state of the manipulating input signal, while outputting the priority of transmitting the manipulating input signal from the master device 9.

The method of determining the priority is not limited to the method described above. For example, instead of determining the priority according to the processing time estimated to be finally required for carrying out all the steps by each of the first to third slave robots 10a-10c, it may be configured to determine the priority according to the delay time of the work at the present time point of each of the first to third slave robots 10a-10c.

Moreover, if the timings at which the first to third slave robots 10a-10c become in the standby state of the manipulating input signal are the same, the priority may be determined so that a higher priority is given to the slave robot 10 which takes charge of an upper stream process of the work.

Moreover, if the timings at which the first to third slave robots 10a-10c become in the standby state of the manipulating input signal are different from each other, the priority may be determined so that a higher priority is given to the salve arm with a longer time in the standby state of the manipulating input signal.

As described above, one example in which the slave robot 10 is in the standby state of the manipulating input signal, the state where the slave robot 10 stands by for the manipulating input signal containing the information indicative of whether or not the continuation is to be permitted, which is transmitted from the master device 9, is illustrated, but it is not limited to this configuration. For example, when the continuation determinator 46 of the slave robot 10 determines that the continuation of the automatic mode is not permitted, it may be in the state where the slave robot 10 stands by for the manipulating input signal containing the information which specifies the operating mode, which is inputted through the master device 9. Alternatively, it may be in the state where the slave robot 10 stands by for the manipulating input signal transmitted to the slave robot 10 through the master device 9 in order to operate the slave arm 1 in the manual mode. That is, in order to receive a certain instruction from an operator, it includes various cases where the slave robot 10 is in the standby state of the manipulating input signal.

Moreover, the slave robot 10 in the standby state of the manipulating input signal may include the slave robot 10 which fell into an abnormal state and, thus, stands by for the manipulating input signal from the master device 9 in order to resume from the abnormal state to a normal state. In such a case, the management control device 20 may determine the priority so that the manipulating input signal is transmitted while giving the priority to the slave robot 10 in the abnormal state among the first to third slave robots 10a-10c in the standby state of the manipulating input signal.

Note that the management control device 20 is capable of grasping whether the slave robot 10 is in the abnormal state, for example, as follows. That is, the management control device 20 is capable of grasping whether the first to third slave robots 10a-10c are in the abnormal state based on, for example, the information indicative of the position and/or posture of the slave arm 1 in the workspace at the present time point, and the information related to the position and/or posture of the slave arm 1 which are planned at the present time point stored in the storage device 6 beforehand, which are acquired by the situation information acquisition part 5. For example, if the slave arm 1 is not on the planned route, or is deviated from the planned route for more than the given range, the management control device 20 is capable of determining that the slave robot 10 is in the abnormal state.

Moreover, the management control device 20 is also capable of grasping that the slave robot 10 fell in the abnormal state, for example, by receiving from the slave robot 10 an abnormal stop signal indicative of that the slave robot 10 stopped due to the abnormality.

It is apparent for a person skilled in the art that many improvements and other embodiments of the present disclosure are possible from the above description. Therefore, the above description is to be interpreted only as illustration, and it is provided in order to teach a person skilled in the art the best mode which implements the present disclosure. Details of the structures and/or the functions of the present disclosure may be substantially changed without departing from the spirit of the present disclosure.

INDUSTRIAL APPLICABILITY

As described above, the robot system 100 according to the present disclosure is widely applicable to systems which act as the plurality of slave robots.

DESCRIPTION OF REFERENCE CHARACTERS

1 Slave Arm
2 Master Arm

3 Control Device
4 Output Device
5 Situation Information Acquisition Part
6 Storage Device
7 Manipulating Instruction Part
9 Master Device
10 Slave Robot
10a First Slave Robot
10b Second Slave Robot
10c Third Slave Robot
20 Management Control Device
40 Receiver
41 Motion Controller
42 Output Controller
46 Continuation Determinator
51 Operation Sequence Information
100 Robot System
101 Robot System

What is claimed is:

1. A robot system comprising:
a master device configured to receive a manipulating instruction from an operator and transmit the received manipulating instruction as a manipulating input signal;
a plurality of slave robots configured to operate according to the manipulating input signal transmitted from the master device;
a management control device configured to manage operations of each slave robot of the plurality of slave robots, respectively, the management control device being configured to:
acquire situation information indicating a situation of each slave robot of the plurality of slave robots in a workspace, respectively,
determine a priority of transmitting the manipulating input signal based on the acquired situation information of each slave robot of the plurality of robots, the manipulating input signal being transmitted from the master device to each slave robot of the plurality of slave robots, which are in a standby state of the manipulating input signal, and
transmit information related to the determined priority; and
an output device configured to output information related to the determined priority transmitted from the management control device to an operator of the robot system.

2. The robot system of claim 1, wherein the management control device is configured to:
acquire a lapsed time of a work being carried out by each slave robot of the plurality of slave robots as the situation information,
calculate a delay time of the work of each slave robot of the plurality of slave robots at a present time point based on the acquired lapsed time of the work, and
according to the calculated delay time, determine the priority of transmitting the manipulating input signal.

3. The robot system of claim 1, wherein the management control device is configured to:
acquire, as the situation information, at least one of information indicating a position and information indicating a posture of each slave robot of the plurality of slave robots in the workspace,
determine whether each slave robot of the plurality of slave robots is in an abnormal state based on the at least one of the information indicating the position and the information indicating the posture of each slave robot of the plurality of slave robots, and
according to the determination, determine the priority of transmitting the manipulating input signal.

4. The robot system of claim 2, wherein the management control device is configured to:
acquire a predetermined planned time required for the work to be performed by each of the plurality of slave robots; and
determine the priority based on a comparison between the calculated delay time and the acquired predetermined planned time.

5. The robot system of claim 4, wherein the management control device is configured to:
based on the comparison between the calculated delay time and the acquired predetermined planned time, calculate an estimated time required from the present time point until completion of the work to be performed by each of the plurality of slave robots; and
determine the priority so as to prioritize the calculated estimated time that is longer among the calculated estimated times of the plurality of slave robots.

* * * * *